(12) United States Patent
Dyker et al.

(10) Patent No.: US 6,900,176 B2
(45) Date of Patent: May 31, 2005

(54) PEST CONTROL AGENTS/DEPSIPEPTIDES

(75) Inventors: Hubert Dyker, Rösrath (DE); Wolfram Andersch, Bergisch Gladbach (DE); Christoph Erdelen, Leichlingen (DE); Peter Lösel, Leverkusen (DE); Ralf Nauen, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/168,382

(22) PCT Filed: Dec. 11, 2000

(86) PCT No.: PCT/EP00/12486

§ 371 (c)(1),
(2), (4) Date: Nov. 13, 2002

(87) PCT Pub. No.: WO01/45512

PCT Pub. Date: Jun. 28, 2001

(65) Prior Publication Data

US 2003/0143254 A1 Jul. 31, 2003

(30) Foreign Application Priority Data

Dec. 22, 1999 (DE) ......................... 199 62 145

(51) Int. Cl.⁷ .................. A01N 43/72; A01N 43/84; C07K 11/02; C07D 273/00
(52) U.S. Cl. .................. 514/11; 514/2; 514/9; 514/16; 514/18; 514/919; 530/317; 530/323; 540/454
(58) Field of Search ............ 514/2, 9, 11, 16, 514/18, 919; 530/317, 323; 540/454

(56) References Cited

U.S. PATENT DOCUMENTS

| | | | |
|---|---|---|---|
| 5,116,815 A | 5/1992 | Takagi et al. | 514/11 |
| 5,380,745 A | 1/1995 | Uomoto et al. | 514/410 |
| 5,514,773 A * | 5/1996 | Nishiyama et al. | 530/317 |
| 5,525,591 A | 6/1996 | Scherkenbeck et al. | 514/18 |
| 5,529,984 A | 6/1996 | Jeschke et al. | 514/17 |
| 5,571,793 A | 11/1996 | Scherkenbeck et al. | 514/19 |
| 5,624,897 A | 4/1997 | Jeschke et al. | 514/11 |
| 5,633,140 A | 5/1997 | Wex et al. | 435/7.1 |
| 5,646,244 A | 7/1997 | Nishiyama et al. | 530/317 |
| 5,663,140 A | 9/1997 | Scherkenbeck et al. | 514/11 |
| 5,717,063 A | 2/1998 | Scherkenbeck et al. | 530/323 |
| 5,747,448 A | 5/1998 | Ohyama et al. | 514/111 |
| 5,773,613 A | 6/1998 | Kawaguchi et al. | 544/246 |
| 5,776,958 A | 7/1998 | Warrellow et al. | 514/345 |
| 5,777,075 A | 7/1998 | Scherkenbeck et al. | 530/330 |
| 5,821,222 A | 10/1998 | Bonse et al. | 514/11 |
| 6,159,932 A | 12/2000 | Mencke et al. | 514/9 |
| 6,265,537 B1 | 7/2001 | Jeschke et al. | 530/317 |
| 6,355,615 B1 | 3/2002 | Dyker et al. | 514/11 |
| 6,369,028 B1 | 4/2002 | Scherkenbeck et al. | 514/9 |

FOREIGN PATENT DOCUMENTS

| | | |
|---|---|---|
| DE | 199 30 076 | 1/2001 |
| EP | 0 634 408 | 1/2000 |
| JP | 8-225552 | 9/1996 |
| WO | 95/27498 | 10/1985 |
| WO | 97/07093 | 2/1997 |
| WO | 99/66794 | 12/1999 |

OTHER PUBLICATIONS

Agric. Biol. Chem. 43 (5), (month unavailable) 1979, pp. 1079–1083, "Syntheses of Bassianolide And its two Homologs, Enniatin C and Decabassianolide", Masaharu Kanaoka, Akira Isogai and Akinori Suzuki.

Database WPI, Week 199346, Derwent Publications Ltd., London, GB; An 1993–365092 XP002163697 & JP 05 271013 A (Meij Seika Kaisha), Oct. 19, 1993 in der Anmeldung er wähnt Zussammenfassung.

* cited by examiner

*Primary Examiner*—John Pak
(74) *Attorney, Agent, or Firm*—Richard E. L. Henderson

(57) ABSTRACT

The present invention relates to the use of 24-membered cyclodepsipeptides of the formula (1)

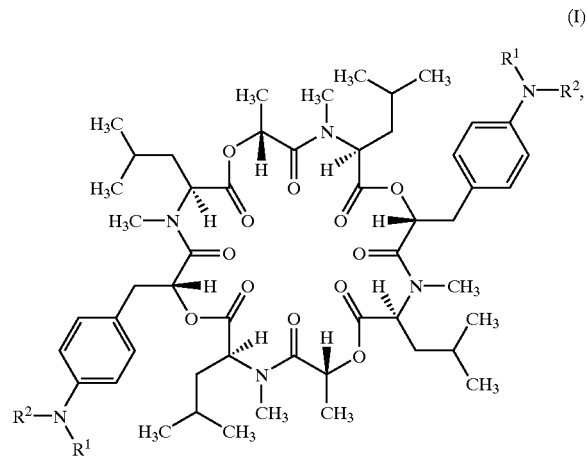

in which $R^1$ and $R^2$ are as defined in the description,
for controlling animal pests in veterinary medicine, hygiene, agriculture, forests and in the protection of materials, to pesticides comprising these depsipeptides and to novel depsipeptides of the formula (1).

5 Claims, No Drawings

PEST CONTROL AGENTS/DEPSIPEPTIDES

This application is a 371 of PCT/EP00/12486, which was filed on Dec. 11, 2000.

The present invention relates to the use of certain 24-membered cyclodepsipeptides for controlling animal pests in veterinary medicine, hygiene, agriculture, forests and in the protection of materials, and to pesticides comprising these depsipeptides.

Cyclic depsipeptides, and their preparation and use as parasiticides against helminths, nematodes and trematodes in animals (endoparasiticides) have already been the subject of numerous publications.

Known is, for example, a cyclodepsipeptide with the name PF 1022 and its action against endoparasites (EP-A 382 173 and EP-A 503 538). Further cyclic depsipeptides (cyclooctadepsipeptides: WO 98/55 469; WO 98/43 965; WO 93/19 053; EP-A 634 408; WO 94/19 334; WO 95/07 272; EP-A 626 375; EP-A 626 376; EP-A 664 297; EP 634 408; EP-A 718 298; WO 97/09 331; cyclohexadepsipeptides: WO 93/25 543; WO 95/27 498; EP-A 658 551; cyclotetradepsipeptides: EP-A 664 297; dioxomorpholines: WO 96/38 165; JP 08 225 552) and open-chain depsipeptides (EP-A 657 171; EP-A 657 172; EP-A 657 173; WO 97/07 093) and their endoparasiticidal action have been described.

Furthermore, it is already known that certain 24-membered cyclodepsipeptides, for example bassianolide and PF1022A, have insecticidal activity against silkworms (cf. M. Kanaoka et al., Agric. Biol. Chem. 43 (5), 1979, pp. 1079–83; JP 05 271 013).

However, the insecticidal activity of these prior-art compounds is, in particular at low application rates and concentrations, not entirely satisfactory in all areas of use.

The invention relates to a composition for controlling animal pests, characterized in that it comprises at least one compound of the formula (I)

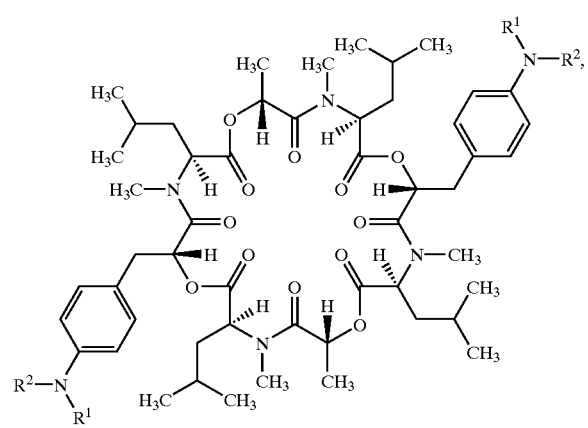

(I)

in which
R$^1$ and R$^2$ each represent alkyl, alkenyl, ω-alkoxyalkyl, ω-halogenoalkyl, optionally substituted arylalkyl or
R$^1$ and R$^2$ together with the nitrogen atom to which they are attached also represent an optionally substituted mono- to tricyclic, optionally bridged, saturated or unsaturated heterocycle which may contain one to three further heteroatoms from the group consisting of nitrogen, oxygen and sulphur, where these radicals in principle are in each case attached to the nitrogen atom via a saturated carbon atom, except for morpholino (R$^1$ and R$^2$=—CH$_2$—CH$_2$—O—CH$_2$—CH$_2$—).

Depending on the type of substituents, the compounds of the general formula (I) can occur as geometrical and/or optical isomer mixtures of varying composition. The invention relates both to the pure isomers and to the isomer mixtures.

The formula (I) provides a general definition of the 24-membered cyclodepsipeptides which can be used according to the invention.

R$^1$ and R$^2$ each preferably represent C$_{1-6}$-alkyl, C$_{2-6}$-alkenyl, ω-C$_{1-4}$-alkoxy-C$_{1-6}$-alkyl, ω-fluoro-C$_{1-6}$-alkyl, ω-chloro-C$_{1-6}$-alkyl, ω-bromo-C$_{1-6}$-alkyl, phenyl-C$_{1-6}$-alkyl which is optionally mono- to trisubstituted by fluorine, chlorine, methyl, methoxy.

R$^1$ and R$^2$ also preferably represent, together with the nitrogen atom to which they are attached, a mono- or bicyclic, optionally bridged, saturated or unsaturated heterocycle which may contain one or two further heteroatoms from the group consisting of nitrogen, oxygen and sulphur and which is optionally substituted by C$_{1-4}$-alkyl, optionally substituted phenyl or phenoxymethyl or by C$_{1-4}$-alkylcarbonyl, where in principle these radicals are in each case attached to the nitrogen atom via a saturated carbon atom, except for morpholino (R$^1$ and R$^2$=—CH$_2$—CH$_2$—O—CH$_2$—CH$_2$—).

R$^1$ and R$^2$ each particularly preferably represent C$_{1-4}$-alkyl, allyl, 2-butenyl, ω—C$_{1-2}$-alkoxy-C$_{1-4}$-alkyl, ω-chloro-C$_{1-4}$-alkyl, ω-bromo-C$_{1-4}$-alkyl or benzyl which is optionally mono- to trisubstituted by fluorine, chlorine, methyl, methoxy.

R$^1$ and R$^2$ also particularly preferably represent, together with the nitrogen atom to which they are attached, morpholino which is mono- or disubstituted by C$_{1-4}$-alkyl, phenoxymethyl, phenyl, tolyl, xylyl, fluorophenyl or chlorophenyl, morpholino which is 2,6- or 3,5-bridged by —CH$_2$—, —(CH$_2$)$_2$— or —(CH$_2$)$_3$—, represent 1-pyrrolidinyl, 1-piperidinyl, 1-piperazinyl, hexahydro-1-pyrazinyl, 4-tetrahydro-1,4-thiazin-1-yl, hexahydro-1,5-oxazocin-5-yl, optionally mono- or disubstituted by C$_{1-4}$-alkyl, phenoxymethyl, phenyl, tolyl, xylyl, fluorophenyl or chlorophenyl, where nitrogen may optionally be substituted by C$_{1-4}$-alkylcarbonyl.

R$^1$ and R$^2$ each very particularly preferably represent methyl, ethyl, n-propyl, isopropyl, n-butyl, isobutyl, tert-butyl, allyl, 2-butenyl, 2-methoxyethyl, 2-ethoxyethyl, 3-methoxy-1-propyl, 4-methoxy-1-butyl, 2-chloroethyl, 3-chloro-1-propyl, 4-chloro-1-butyl, 2-bromoethyl, 3-bromo-1-propyl, 4-bromo-1-butyl or benzyl.

R$^1$ and R$^2$ also very particularly preferably represent, together with the nitrogen atom to which they are attached, 1-pyrrolidinyl, 1-piperidinyl, 3,5-dimethylmorpholino, 2-phenoxymethylmorpholino, 3-phenylmorpholino, 3-aza-8-oxa-bicyclo[3.2.1]oct-3-yl, 4-acetyl-1-piperazinyl, 4-tetrahydro-1,4-thiazin-1-yl or hexahydro-5-oxazocin-5-yl.

The abovementioned general or preferred radical definitions or illustrations can be combined with one another as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Saturated or unsaturated hydrocarbon radicals, such as alkyl or alkenyl, can in each case be straight-chain or branched, including in combination with heteroatoms, such as, for example, in alkoxy, if possible.

Optionally substituted radicals can be mono- or polysubstituted, and, in the case of polysubstitutions, the substituents can be identical or different.

Some of the active compounds which can be used according to the invention are known. Their preparation is described in the literature mentioned above.

The novel compounds of the formula (I) likewise form part of the subject-matter of this application.

Furthermore, we have found a process for preparing the compounds of the formula (I)

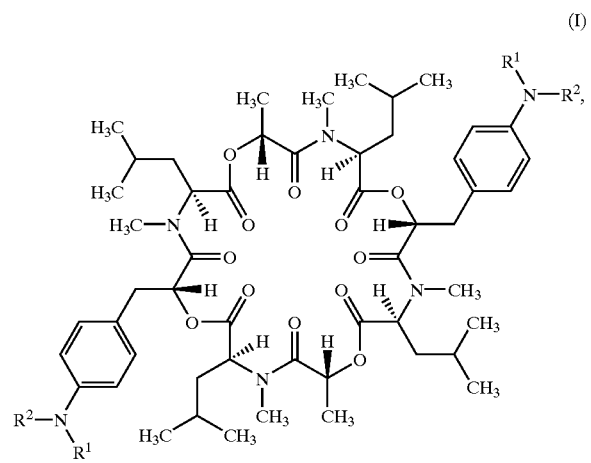

in which $R^1$ and $R^2$ are as defined above, characterized in that a compound of the formula (II)

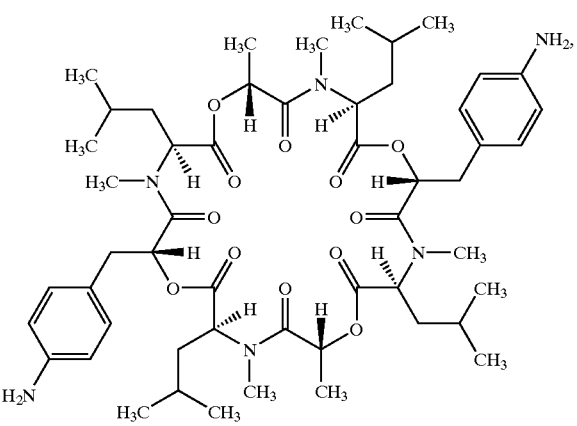

in the case that the radicals $R^1$ and $R^2$ are not linked, is reacted with compounds of the formula (III-a)

$$R^{1-1}-X \qquad (\text{III-a}),$$

in which $R^{1-1}$ has the meanings mentioned in the definition of the formula (I) for $R^1$ and $R^2$, and in the case that the radicals $R^1$ and $R^2$, as indicated in the definition of the formula (I), are linked, is reacted with compounds of the formula (III-b)

$$X-A-X \qquad (\text{III-b}),$$

in which

A represents an optionally substituted α, ω-alkylene radical which may also be mono- or bicyclically bridged and, with the exception of the atoms which are attached to the radicals X and which are saturated carbon atoms, may contain one to three further heteroatoms from the group consisting of nitrogen, oxygen and sulphur, and X in the formulae (III-a) and (III-b) represents a leaving group, such as, for example, chlorine, bromine, iodine, methylsulphonyloxy, trifluoromethyl-sulphonyloxy or tolylsulphonyloxy, in the presence of an acid binder and, if appropriate, a diluent and, if appropriate, a reaction auxiliary.

Here, A preferably and particularly preferably represents the radicals which are analogous to the meanings of $R^1$ and $R^2$ in the definition of the formula (I).

Using, for example, 3-chloropropyl triflate (and bis-amino compound of the formula (II)) as starting materials, the course of the reaction of the process can be represented by the following formula scheme:

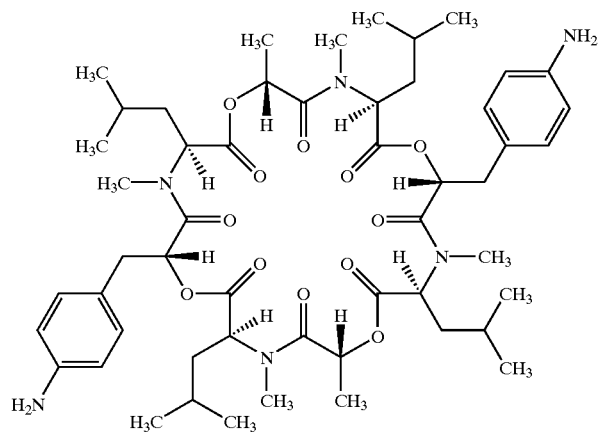

+

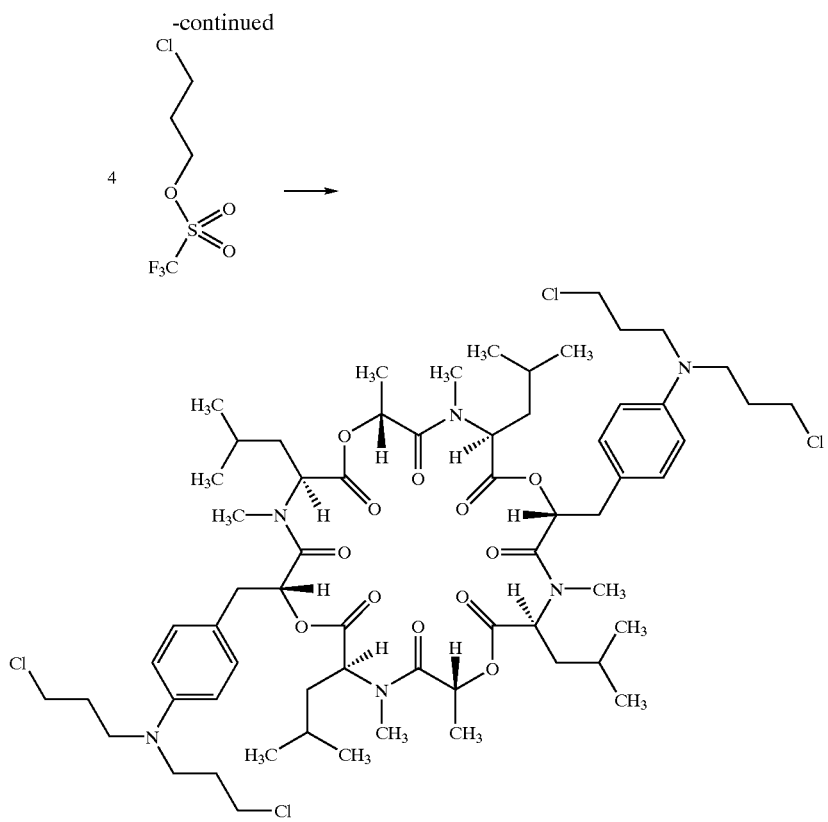

The diamine of the formula (II) required for carrying out the process is known, inter alia, from EP-A 872 481 and can be prepared as described therein.

The formulae (III-a) and (III-b) provide general definitions of the other compounds that are required. In these formulae, $R^1$ and A are preferably analogous to the preferred definitions of the radicals $R^1$ and $R^2$ in the definition of the compounds of the formula (I) which can be used according to the invention.

The compounds of the formulae (III-a) and (III-b) are commercially available, known or can be prepared by generally known methods of organic chemistry (see also Jerry March, Advanced Organic Chemistry, Wiley Interscience, etc.).

Suitable acid acceptors for carrying out the process are customary inorganic or organic bases. These preferably include alkaline earth metal or alkali metal acetates, carbonates or bicarbonates, such as, for example, sodium acetate, potassium acetate, calcium acetate or ammonium acetate, sodium carbonate, potassium carbonate or ammonium carbonate, sodium bicarbonate or potassium bicarbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylamino-pyridine, diazabicyclooctane (DABCO), diazabicyclononene (DBN) or diazabicycloundecene (DBU). Preference is given to using sodium carbonate, potassium carbonate or caesium carbonate, sodium bicarbonate or potassium bicarbonate, triethylamine, diisopropylethylamine or N-methylmorpholine.

The process is preferably carried out in the presence of a diluent. Suitable diluents are water, organic solvents and any mixtures thereof. Examples which may be mentioned are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloro-, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; ketones, such as acetone, butanone, methyl isobutyl ketone or cyclohexanone; nitriles, such as acetonitrile, propionitrile, n- or i-butyronitrile or benzonitrile; amides, such as formamide, N,N-dimethylforamide, N,N-dimethylacetamide, N-methylformanilide, N-methylpyrrolidone or hexamethylphosphoric triamide; N-oxides, such as N-methylmorpholine N-oxide; esters, such as methyl acetate, ethyl acetate or butyl acetate; sulphoxides, such as dimethyl sulphoxide; sulphones, such as sulpholane; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether; water. Preference is given to propionitrile, acetonitrile, dimethylformamide, dimethyl sulphoxide, dichloromethane.

Suitable reaction auxiliaries are alkali metal halides or quaternary ammonium halides, such as, for example, lithium iodide, sodium iodide or tetrabutylammonium iodide.

When carrying out the process, the reaction temperature can be varied within a relatively wide range. In general, the process is carried out at temperatures between 20° and 150° C., preferably at from 50° to 130° C., particularly preferably at from 800 to 120° C.

When carrying out the process, 4 to 20 mol, preferably 5 to 10 mol, of monofunctional compound of the formula (III-a) or half of the bifunctional compound of the formula (III-b) are employed per mole of the compound of the formula (I). The upper limit of the amount of acid binder employed is not critical. Preferably, the amount that is employed is equivalent to the amount of the compound of the formulae (III). This also applies to the amount of a reaction auxiliary that is to be employed, if appropriate.

The reactions can be carried out at atmospheric pressure or under elevated pressure. They are preferably carried out at atmospheric pressure. The practice of the reaction and the work-up and isolation of the reaction products are carried out by generally customary known methods. The end products are preferably purified by crystallization, chromatographic separation or by removing the volatile components, if appropriate under reduced pressure (cf. also the Preparation Examples).

The active compounds are suitable for controlling animal pests, in particular insects, arachnids and nematodes, which are encountered in agriculture, in forestry, in the protection of stored products and of materials, and in the hygiene field, and are tolerated well by plants and have favourable homeotherm toxicity. Preferably, they can be employed as crop protection agents or as veterinary medicaments for useful animals and pets and in stable and household hygiene. They are active against normally sensitive and resistant species and against all or some stages of development. The above-mentioned pests include:

From the order of Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blatella germanica, Acheta domesticus, Gryllotalpa* spp., *Locusta migratoria migratorioides, Melanoplus differentialis* and *Schistocerca gregaria.*

From the order of the Dermaptera, for example, *Forficula auricularia.*

From the order of the Isoptera, for example, *Reticulitermes* spp.

From the order of the Anoplura, for example, *Pediculus humanus corporis, Haematopinus* spp. and *Linognathus* spp.

From the order of the Mallophaga, for example, *Trichodectes* spp. and *Damalinea* spp.

From the order of the Thysanoptera, for example, *Hercinothrips femoralis* and *Thrips tabaci.*

From the order of the Heteroptera, for example, *Eurygaster* spp., *Dysdercus intermedius, Piesma quadrata, Cimex lectularius, Rhodnius prolixus* and *Triatoma* spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis porni, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotetlix cincticeps, Lecanium comi, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp, *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus suinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon soistitialis* and *Costelytra zealandica.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa.*

From the order of the Siphonaptera, for example, *Xenopsylla cheopis* and *Ceratophyllus* spp.

From the order of the Arachnida, for example, *Scorpio maurus* and *Latrodectus mactans.*

From the order of the Acarina, for example, *Acarus siro, Argas* spp., *Omithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroples* spp., *Chorioptes* spp., *Sarcoptes* spp., *Tarsonemus* spp., *Bryobia praetiosa, Panonychus* spp. and *Tetranychus* spp.

The phytoparasitic nematodes include *Pratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphinema* spp. and *Trichodorus* spp.

The active compounds of the formula (I) which can be used according to the invention are particularly distinguished by an excellent activity against lepidoptera such as the caterpillars of *Spodoptera frugiperda* and *Heliothis virescens.*

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

As solid carriers there are suitable:
for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite and also synthetic granules of inorganic and organic meals, and granules of organic material such as sawdust, coconut shells, maize cobs and tobacco stalks; as emulsifiers and/or foam-formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates and also protein hydrolysates; as dispersing agents there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound according to the invention can be present in its commercially available formulations and in the use forms prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms.

Examples of particularly advantageous mixture components are the following compounds:

Fungicides:
2-aminobutane; 2-anilino-4-methyl-6-cyclopropyl-pyrimidine; 2,6'-dibromo-2-methyl-4'-trifluoromethoxy-4'-trifluoro-methyl-1,3-thiazole-5-carboxanilide; 2,6-dichloro-N-(4'-trifluoromethylbenzyl)-benzamide; (E)-2-methoxyimino-N-methyl-2-(2-phenoxy-phenyl)-acetamide; 8-hydroxyquinoline sulphate; methyl (E)-2-[2-[6-(2-cyano-phenoxy)pyrimidin-4-yloxy]-phenyl]-3-methoxyacrylate; methyl (E)-methoximino-[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diacloden, diafenthiuron, diazinon, dichlorvos, diflubenzuron, dimethoat, dimethylvinphos, diofenolan, disulfoton, docusat-sodium, dofenapyn, eflusilanate, emamectin, empenthrin, endosulfan, *Entomopfthora* spp., epripomectin, esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, lambda-cyhalothrin, lufenuron, malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos, moxidectin, naled, nitenpyram, nithiazine, novaluron, nuclear polyhedrosal viruses, omethoat, oxamyl, oxydemethon M,

*Paecilomyces fumosoroseus*, parathion A, parathion M, permethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen, quinalphos, ribavirin, salithion, sebufos, selamectin, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,

YI 5302, zeta-cypermethrin, zolaprofos, (1R-cis)-[5-(phenylmethyl)-3-furanyl]-methyl-3-[(dihydro-2-oxo-3-(2H)-furanylidene)-methyl] 2,2-dimethylcyclopropanecarboxylate, (3-phenoxyphenyl)-methyl 2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydrooxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)-methoxy]-3 (2H)-pyridazinone, 4-chloro-5-[(6-chloro-3-pyridinyl)methoxy]-2-(3,4-dichlorophenyl)-3(2H)-pyridazinone, Bacillus thuringiensis strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4-trifluoro-1-oxo-3-butenyl)-glycine, N-(4-chlorophenyl)-3-[4-(difluoromethoxy)phenyl]4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

It is also possible to admix other known active compounds, such as herbicides, fertilizers and growth-regulating substances.

The active compounds according to the invention can furthermore be present in their commercially available formulations and in the use forms prepared from these formulations, as a mixture with synergistic agents. Synergistic agents are compounds which increase the action of the active compounds without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds have excellent residual action on wood and clay and also good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example and *Haematopinus* spp., *Linognathus* spp., *Pediculus* spp., *Phtirus* spp. *Solenopotes* spp.

From the order of the Mallophagida and the sub-orders Amblycerina and Ischnocerina, for example *Trimenopon* spp., *Menopon* spp., *Trinoton* spp., *Bovicola* spp., *Wemeckiella* spp., *Lepikentron* spp., *Damalina* spp., *Trichodectes* spp. and *Felicola* spp.

From the order Diptera and the sub-orders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaca* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp.

From the sub-class of the Acaria (Acarida) and the orders of the Meta- and Mesostigmata, for example *Argas* spp., *Omithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Octodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals such as, for example, hamsters, guinea-pigs, rats and mice. By controlling these arthropods, it is intended to reduce mortality and decreased performance (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 8% by weight, either directly or after dilution by a factor of 100 to 10 000, or they may be used in the form of a chemical bath.

Furthermore, it has been found that the compounds of the formula (I) according to the invention have potent insecticidal action against insects which destroy industrial materials.

The following insects may be mentioned by way of example and as being preferred, but without any limitation:

Beetles, such as

*Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Hymenoptera, such as

*Sirex juvencus, Urocerus gigas, Urocerus gigas tacgnus, Urocerus augur.*

Termites, such as

*Kalotermes flavicollis, Cryptotermes brevis, Heterotermes indicola, Reticulitermes flavipes, Reticulitermes santonensis, Reticulitemes lucifugus, Mastotermes darwiniensis, Zootermopsis nevadensis, Coptoternes formosanus.*

Bristletails, such as *Lepisma saccharina.*

Industrial materials are to be understood as meaning, in the present context, non-live materials such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water with, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the, synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of the binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylene benzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise further insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorofluanide, tolylfluamide, 3-iodo-2-propinyl-butyl carbamate, N-octyl-isothiazolin-3-one and 4,5-dichloro-N-octylisothiazolin-3-one.

The active compounds are also suitable for controlling animal pests, in particular insects, arachnids and mites, which are encountered in closed rooms, such as, for example, flats, factory halls, offices, vehicle cabins and the like. They can be used alone or in combination with other active compounds and auxiliaries in household insecticidal products for controlling these pests. They are active against sensitive and resistant species and against all stages of development. These pests include:

From the order of the *Scorpionidea*, for example *Buthus occitanus*.

From the order of the Acarina, for example *Argas persicus, Argas reflexus, Bryobia* ssp., *Dermnanyssus gallinae, Glyciphagus domesticus, Omithodorus moubat, Rhipicephalus sanguineus, Trombicula alfreddugesi, Neutrombicula autumnalis, Dermatophagoides pteronissimus, Dermatophagoides forinae*.

From the order of the *Araneae*, for example *Aviculariidae, Araneidae*.

From the order of the *Opiliones*, for example *Pseudoscorpiones chelifer, Pseudoscorpiones cheiridium, Opiliones phalangium*.

From the order of the Isopoda, for example *Oniscus asellus, Porcellio scaber*.

From the order of the Diplopoda, for example *Blaniulus guttulatus, Polydesmus* spp.

From the order of the *Chilopoda*, for example *Geophilus* spp.

From the order of the *Zygentoma*, for example *Ctenolepisma* spp., *Lepisma saccharina, Lepismodes inquilinus*.

From the order of the *Blattaria*, for example *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the *Saltatoria*, for example *Acheta domesticus*.

From the order of the *Dermaptera*, for example *Forficula auricularia*.

From the order of the *Isoptera*, for example *Kalotermes* spp., *Reticulitermes* spp.

From the order of the *Psocoptera*, for example *Lepinatus* spp., *Liposcelis* spp.

From the order of the *Coleptera*, for example *Anthrenus* spp., *Attagenus* spp., *Dermestes* spp., *Latheticus oryzae*, *Necrobia* spp., *Ptinus* spp., *Rhizopertha dominica*, *Sitophilus granarius*, *Sitophilus oryzae*, *Sitophilus zeamais*, *Stegobium paniceum*.

From the order of the Diptera, for example *Aedes aegypti*, *Aedes albopictus*, *Aedes taeniorhynchus*, *Anopheles* spp., *Calliphora erythrocephala*, *Chrysozona pluvialis*, *Culex quinquefasciatus*, *Culex pipiens*, *Culex tarsalis*, *Drosophila* spp., *Fannia canicularis*, *Musca domestica*, *Phlebotomus* spp., *Sarcophaga carnaria*, *Simulium* spp., *Stomoxys calcitrans*, *Tipula paludosa*.

From the order of the Lepidoptera, for example *Achroia griselia*, *Galleria mellonella*, *Plodia interpunctella*, *Tinea cloacella*, *Tinea pellionella*, *Tineola bisselliella*.

From the order of the Siphonaptera, for example *Ctenocephalides canis*, *Ctenoccphalides felis*, *Pulex irritans*, *Tunga penetrans*, *Xenopsylla cheopis*.

From the order of the Hymenoptera, for example *Camponotus herculeanus*, *Lasius fuliginosus*, *Lasius niger*, *Lasius umbratus*, *Monomorium pharaonis*, *Paravespula* spp., *Tetramorium caespitum*.

From the order of the Anoplura, for example *Pediculus humanus capitis*, *Pediculus humanus corporis*, *Phthirus pubis*.

From the order of the Heteroptera, for example *Cimex hemipterus*, *Cimex lectularius*, *Rhodinus prolixus*, *Triatoma infestans*.

In the field of the household insecticides, they are used alone or in combination with other suitable active compounds, such as phosphoric acid esters, carbamates, pyrethroids, growth regulators or active compounds from other known classes of insecticide.

They are used in the form of aerosols, unpressurized sprays, for example pump and atomizer sprays, nebulizers, foggers, foams, gels, vaporizer products with vaporizer tablets made of cellulose or plastic, liquid vaporizers, gel and membrane vaporizers, propeller-operated vaporizers, energyless or passive vaporizer systems, moth papers, moth sachets and moth gels, as granules or dusts, in baits for scattering or bait stations.

The preparation and the use of the active compounds according to the invention are shown in the examples below.

EXAMPLES

General Procedure 0.979 g (1.00 mmol) of bis-amino compound of the formula (II), 6,18-di-(4-amino-benzyl)-3,9,15,21-tetraisobutyl-4,10,12,16,22,24-hexamethyl-1,7,13,19-tetraoxa-4,10,16,22-tetraaza-cyclotetracosan-2,5,8,11,14, 17,20,23-octaone and 3.8 mmol of bistosylate (corresponds to formula (III-b); prepared from the corresponding diol) in 10 ml of propionitrile are reacted at 100° C. in the presence of 0.40 g (3.8 mmol) of sodium carbonate and 1.40 g (3.8 mmol) of tetra(n-butyl)ammonium iodide for 5 to 12 h.

For work-up, the reaction solution is diluted with ethyl acetate and washed with half-saturated ammonium chloride solution, saturated sodium bicarbonate solution and saturated sodium chloride solution. The organic phase is dried over magnesium sulphate and concentrated under reduced pressure. The product is purified by column chromatography (stationary phase: silica gel; mobile phase: ethyl acetate/cyclohexane).

Examples 1–9

The following compounds of the formulae (I-1) to (I-9) were prepared according to the general procedure.

TABLE 1

| Example No. (n) | —NR$^1$R$^2$ | MS: [m/z] M$^+$H/M$^+$ + Na | Yield [of theory] |
|---|---|---|---|
| 1 | 3,5-dimethylmorpholinyl | 1175/1198 | 26% |
| 2 | pyrrolidinyl | 1087/1109 | 67% |
| 3 | 1,4-oxazocanyl | 1175/1197 | 26% |
| 4 | piperidinyl | 115/1137 | 40% |
| 5 | thiomorpholinyl | 1151/1173 | 59% |
| 6 | 8-methyl-3-oxa-8-azabicyclo | 1171/1188 (M$^+$ + NH$_4$)/1193 | 51% |
| 7 | 2-phenoxymethyl-morpholinyl | 1131/— | 20% |
| 8 | 3-phenyl-morpholinyl (N-methyl) | 1171(M$^+$)/ 1272/1294 | 65% |

TABLE 1-continued

[Structure (I-n) shown: cyclic depsipeptide with R¹, R² substituents on aryl nitrogens]

| Example No. (n) | —NR¹R² | MS: [m/z] M⁺H/M⁺ + Na | Yield [of theory] |
|---|---|---|---|
| 9 | —N(piperazinyl)N-C(=O)CH₃ | 1201/1223 | 36% |

BIOLOGICAL EXAMPLES

Example A
*Heliothis Virescens* Test

Solvent: 3 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Soya bean shoots (*Glycine max*) are treated by being dipped into the preparation of active compound of the desired concentration and are populated with *Heliothis virescens* caterpillars while the leaves are still moist.

After the desired period of time, the kill in % is determined. 100% means that all caterpillars have been killed; 0% means that none of the caterpillars has been killed.

In this test, for example, the following compounds of the Preparation Examples show good activity:

| Example | Concentration of active compound ppm | Kill rate in % after 6 days |
|---|---|---|
| 1 | 200 | 100 |
| 2 | 1000 | 100 |
| 3 | 1000 | 100 |

Example B
Phaedon Larvae Test

Solvent: 3 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (Phaedon cochleariae) while the leaves are still moist.

After the desired period of time, the kill in % is determined. 100% means that all beetle larvae have been killed; 0% means that none of the beetle larvae has been killed.

In this test, for example, the following compounds of the Preparation Examples show good activity:

| Example | Concentration of active compound ppm | Kill rate in % after 6 days |
|---|---|---|
| 1 | 200 | 100 |
| 3 | 200 | 100 |

Example C
*Plutella* Test

Solvent: 3 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamondback moth (*Plutella xylostella*) while the leaves are still moist.

After the desired period of time, the kill in % is determined. 100% means that all caterpillars have been killed; 0% means that none of the caterpillars has been killed.

In this test, for example, the following compound of the Preparation Examples shows good activity:

| Example | Concentration of active compound ppm | Kill rate in % after 6 days |
|---|---|---|
| 3 | 1000 | 100 |

Example D
*Plutella* Test/Synthetic Feed

Solvent: 1 part by weight of acetone
9 parts by weight of methanol

To produce a suitable preparation of active compound, 1 part by weight of active compound is mixed with the stated amount of solvent, and the concentrate is diluted with methanol to the desired concentrations.

A stated amount of the preparation of active compound of the desired concentration is pipetted onto a standardized amount of synthetic feed. After the methanol has evaporated, a film box lid covered with approximately 100 *Plutella* eggs is placed onto each cavity. The freshly hatched larvae migrate onto the treated synthetic feed.

After the desired period of time, the kill in % is determined. 100% means that all animals have been killed; 0% means that none of the animals has been killed.

In this test, for example, the following compounds of the Preparation Examples show good activity:

| Example | Concentration of active compound in ppm | Kill rate in % after 6 days |
|---------|------------------------------------------|------------------------------|
| 5       | 1000                                     | 100                          |

Example E
*Plutella* Test/Symptomatology Study
Solvent: Acetone

To produce a suitable preparation of active compound, 10 mg of active compound are mixed with 1 ml of solvent.

1 µl of the solution prepared in this manner is administered to caterpillars of the diamondback moth (*Plutella xylostella*).

After the desired period of time, the kill in % is determined. 100% means that all caterpillars have been killed; 0% means that none of the caterpillars has been killed.

In this test, for example, the following compounds of the Preparation Examples show good activity:

| Example | Concentration of active compound in µg/larvae | Kill rate in % after 1 day |
|---------|------------------------------------------------|-----------------------------|
| 1       | 10                                             | 100                         |

Example F
*Spodoptera Frugiperda* Test
Solvent: 31 parts by weight of acetone
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars has been killed.

In this test, for example, the following compounds of the Preparation Examples show good activity:

| Example | Concentration of active compound in ppm | Kill rate in % after 6 days |
|---------|------------------------------------------|------------------------------|
| 1       | 1000                                     | 100                          |
| 2       | 1000                                     | 100                          |
| 3       | 1000                                     | 100                          |

Example G
*Tetranychus* Test (OP-Resistant/Dip Treatment)
Solvent: 7 parts by weight of dimethylformamide
Emulsifier: 1 part by weight of alkylaryl polyglycol ether To produce a suitable preparation of active compound, 1 part by weight of active compound is mixed with stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % is determined. 100% means that all spider mites have been killed; 0% means that none of the spider mites has been killed.

In this test, for example, the following compounds of the Preparation Examples show good activity:

| Example | Concentration of active compound in ppm | Kill rate in % after 7 days |
|---------|------------------------------------------|------------------------------|
| 1       | 200                                      | 100                          |
| 3       | 200                                      | 99                           |

Example H
*Meloidogyne* Test
Solvent: 4 parts by weight of acetone
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Containers are filled with sand, solution of active compound, *Meloidogyne incognita* egg/larvae suspension and lettuce seeds. The lettuce seeds germinate and the plants develop. Galls form on the roots.

After the desired period of time, the nematicidal activity is determined by the gall formation in %. 100% means that no galls have been found; 0% means that the number of galls on the treated plants corresponds to that of the untreated control.

Active compounds, application rates and results are shown in the table below:

| Example | Concentration of active compound in ppm | Kill rate in % |
|---------|------------------------------------------|-----------------|
| 1       | 20                                       | 100             |
| 3       | 20                                       | 100             |

Example I
Cockroach Test

Test animals: Larvae (IA) of *Periplaneta americana*
Solvent: Dimethyl sulphoxide 20 mg of active compound are dissolved in 1 ml of dimethyl sulphoxide, more dilute concentrations are prepared by dilution with distilled water.

4 test animals are dipped for 1 minute into the preparation of active compound to be tested.

The animals are transferred into plastic beakers and kept in a climatized room for 7 days, and the kill rate is then determined.

100% means that all cockroaches have been killed, 0% means that none of the cockroaches has been killed.

In this test, for example, the following compounds of the Preparation Examples are superior to the prior art:

| Example | Concentration of active compound in ppm | % Activity/kill |
|---------|------------------------------------------|------------------|
| 1       | 100                                      | 50               |

Example J

Test with Cat Fleas/Oral Uptake
Test animals: Adult *Ctenocephalides felis*
Solvent: Dimethyl sulphoxide (DMSO)

To prepare a suitable formulation, a suitable solution of active compound is prepared from 20 mg of active compound and 1 ml of DMSO. 17.5 µl of this formulation are added to 3.5 ml of citrated cattle blood, and the mixture is stirred.

20 unfed adult fleas (*Cienocephalides felis*, strain "Georgi") are placed into a chamber (Ø2.5 cm) whose top and bottom are closed with gauze. A metal cylinder whose underside is covered with parafilm is placed onto the chamber. The cylinder contains 3 ml of blood/active compound formulation which can be taken up by the fleas through the parafilm membrane. Whereas the blood is warmed to 37° C., the temperature in the area of the flea chambers is adjusted to 25° C. Controls are mixed with the same volume of DMSO, without addition of a compound. The determinations are carried out in triplicate.

After 28 h, the mortality in % (=dead fleas) is determined. Compounds which reflect a kill of the fleas of at least 25% within 28 h are judged to be effective.

| Example | Concentration of active compound in ppm | % Activity |
|---|---|---|
| 1 | 100 | 100 |
| 2 | 100 | 91 |
| 3 | 100 | 100 |
| 4 | 100 | 100 |
| 5 | 100 | 64 |
| 6 | 100 | 80 |

Example K

Test with Flies
Test animals: Adult *Musca domestica*, strain Reichswald (OP—, SP—, carbamate-resistant)
Solvent: Dimethyl sulphoxide 20 mg of active compound are dissolved in 1 ml of dimethyl sulphoxide, more dilute concentrations are prepared by dilution with distilled H$_2$O.

2 ml of this preparation of active compound are pipetted onto filter paper discs (Ø9.5 cm) which are located in Petri dishes of a corresponding size. The filter discs are dried, and 25 test animals are then transferred into the Petri dishes and covered.

The activity of the preparation of active compound is determined after 1, 3, 5, 24 and 48 hours. 100% means that all flies have been killed; 0% means that none of the flies has been killed.

In this test, for example, the following compounds of the Preparation Examples are superior to the prior art:

| Example | Concentration of active compound in ppm | % Activity/kill |
|---|---|---|
| 1 | 100 | 95 |
| 3 | 100 | 95 |
| 4 | 100 | 20 |
| 7 | 100 | 20 |

Example L

Test with Cattle Ticks
Test animals: Females of *Boophilus microplus* (SP-resistant Parkhurst strain) which have sucked themselves full
Solvent: Dimethyl sulphoxide 20 mg of active compound are dissolved in 1 ml of dimethyl sulphoxide, more dilute concentrations are prepared by dilution with the same solvent.

The test is carried out in 5 replications. 1 µl of the solutions is injected into the abdomen and the animals are transferred into dishes and kept in a climatized room. The activity is checked after 7 days, for deposition of fertile eggs. Eggs whose fertility is not visibly apparent are kept in glass tubes in a climatized cabinet until the larvae have hatched. An activity of 100% means that no tick has deposited fertile eggs.

In this test, for example, the following compounds of the Preparation Examples are superior to the prior art:

| Example | Concentration of active compound in µg per animal | % Activity/kill |
|---|---|---|
| 1 | 20 | 100 |
| 2 | 20 | 100 |
| 3 | 20 | 100 |
| 4 | 20 | 100 |
| 5 | 20 | 80 |
| 6 | 20 | 100 |

Example M

Blowfly Larvae Test/Development-Inhibitory Action
Test animals: *Lucilia cuprina* larvae
Solvent: Dimethyl sulphoxide 20 mg of active compound are dissolved in 1 ml of dimethyl sulphoxide, more dilute concentrations are prepared by dilution with distilled water.

About 20 *Lucilia* cuprina larvae are introduced into a test tube which contains about 1 cm$^3$ of horse meat and 0.5 ml of the preparation of active compound to be tested. After 24 hours and 48 hours, the effectiveness of the preparation of active compound is determined. The test tubes are transferred into beakers whose bottom is covered with sand. After a further 2 days, the test tubes are removed and the pupae are counted.

The effect of the preparation of active compound is assessed by the number of flies which have hatched after 1.5 times the development period of an untreated control. 100% means that no flies have hatched; 0% means that all flies have hatched normally.

In this test, for example, the following compounds of the Preparation Examples are superior to the prior art:

| Example | Concentration of active compound in ppm | % Activity/kill (after 48 hours) |
|---|---|---|
| 1 | 10 | 100 |
| 3 | 10 | 100 |
| 4 | 100 | 100 |
| 5 | 100 | 100 |
| 6 | 100 | 100 |

What is claimed is:

1. A composition for controlling animal posts comprising a compound of the formula (I)

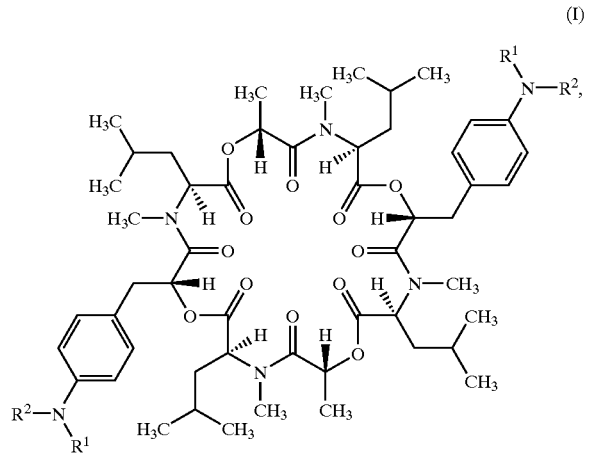

(I)

in which

R$^1$ and R$^2$, together with the nitrogen atom to which they are attached, represent morpholino that is mono- or disubstituted by C$_{1-4}$-alkyl; or represent hexahydro-1, 5-oxazocin-5-yl that is optionally mono- or disubstituted by C$_{1-4}$-alkyl, phenoxymethyl, phenyl, tolyl, xylyl, fluorophenyl, or chlorophenyl.

2. A composition according to claim 1 in which R$^1$ and R$^2$, together with the nitrogen atom to which they are attached, represent morpholino that is disubstituted by C$_{1-4}$-alkyl.

3. A composition according to claim 1 in which R$^1$ and R$^2$, together with the nitrogen atom to which they are attached, represent unsubstituted hexahydro-1,5-oxazocin-5-yl.

4. A method for controlling ectoparasites comprising applying an effective amount of a compound of the formula (I) according to claim 1 to ectoparasites or to a material or animal to be protected from ectoparasites.

5. A method for controlling insects comprising applying an effective amount of a compound of the formula (I) according to claim 1 to an insect or to a material or animal to be protected from insects.

* * * * *